United States Patent
Hushon et al.

(10) Patent No.: US 9,075,668 B1
(45) Date of Patent: Jul. 7, 2015

(54) METHOD, APPARATUS AND SYSTEM FOR INTEGRATING DYNAMIC RECOGNITION OF COMPLEX EVENTS WITH CASE-BASED PROCESSING

(75) Inventors: John Daniel Hushon, Medfield, MA (US); David S. Reiner, Lexington, MA (US); Igor Makhlin, Haifa (IL)

(73) Assignee: EMC Corporation, Hopkinton, MA (US)

( * ) Notice: Subject to any disclaimer, the term of this patent is extended or adjusted under 35 U.S.C. 154(b) by 660 days.

(21) Appl. No.: 12/977,604

(22) Filed: Dec. 23, 2010

(51) Int. Cl.
*G06F 3/00* (2006.01)
*G06F 9/54* (2006.01)

(52) U.S. Cl.
CPC .......................................... *G06F 9/54* (2013.01)

(58) Field of Classification Search
None
See application file for complete search history.

(56) References Cited

U.S. PATENT DOCUMENTS

| | | | | |
|---|---|---|---|---|
| 2006/0085412 A1* | 4/2006 | Johnson et al. | | 707/4 |
| 2006/0229923 A1* | 10/2006 | Adi et al. | | 705/8 |
| 2008/0109824 A1* | 5/2008 | Chen et al. | | 719/318 |
| 2008/0312995 A1* | 12/2008 | Van Wyk et al. | | 705/7 |
| 2009/0138318 A1* | 5/2009 | Hawkins et al. | | 705/9 |
| 2009/0204470 A1* | 8/2009 | Weyl et al. | | 705/9 |

OTHER PUBLICATIONS

"EMC's Case Framework Platform xCP Saves Time and Money", Barb Mosher, www.cmswire.com, Oct. 6, 2009, pp. 3-4.*

* cited by examiner

*Primary Examiner* — Gregory A Kessler
(74) *Attorney, Agent, or Firm* — Ryan, Mason & Lewis, LLP

(57) ABSTRACT

In one aspect, an apparatus for integrating dynamic recognition of complex events with case-based processing comprises at least one processing platform. The processing platform comprises at least one server, computer or other processing device having a processor coupled to a memory. The processing platform implements a plurality of modules for integration of dynamic recognition of complex events with case-based processing, the modules comprising at least a complex event processing module and a case-based processing module coupled to the complex event processing module. Event recognition in the complex event processing module triggers one or more case-based activities in the case-based processing module. The plurality of modules may further include an event preprocessing module, a proactive risk assessment and forecasting module, and a temporal associative reasoning module.

21 Claims, 3 Drawing Sheets

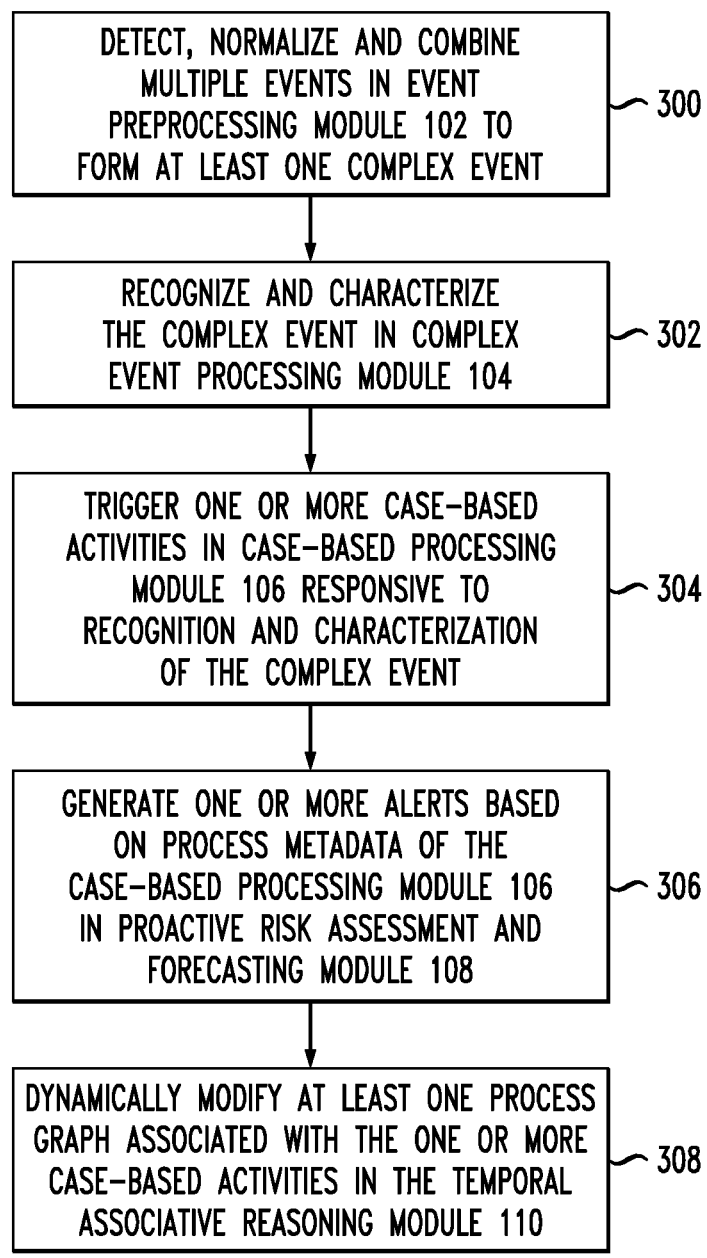

METHOD, APPARATUS AND SYSTEM FOR INTEGRATING DYNAMIC RECOGNITION OF COMPLEX EVENTS WITH CASE-BASED PROCESSING

FIELD OF THE INVENTION

The present invention relates generally to the field of information processing, and more particularly to techniques for implementing dynamic event recognition in an information processing system.

BACKGROUND OF THE INVENTION

Event processing systems are coming into increasingly widespread use in a variety of different enterprises. However, existing event processing systems have a number of significant drawbacks. For example, such systems often require custom-built transformations for each different type of input event information to be processed, and are generally unable to detect, normalize and combine event information from multiple federated information sources. Also, the existing event processing systems are typically very limited in terms of the complexity of events that can be recognized and processed.

A given enterprise may therefore have to combine multiple disparate event processing systems in order to handle complex events. In addition, exception handling in such arrangements often requires extensive human intervention. As a result, the deployment of complex event processing functionality can be unduly expensive and time-consuming for the enterprise.

The above-noted drawbacks are becoming increasingly problematic as virtual infrastructure becomes more widely distributed over larger numbers of physical machines. For example, commercially available virtualization software such as VMware® vSphere™ may be used to build a variety of different types of virtual infrastructure, including private and public cloud computing and storage systems, distributed across hundreds of interconnected physical computers and storage devices. As the complexity of such cloud-based systems increases, the need for accurate and efficient event processing has also grown. Unfortunately, existing event processing systems are not easily able to accommodate this increasing complexity of enterprise infrastructure.

Accordingly, a need exists for an improved approach to the detection and processing of complex events in an information processing system.

SUMMARY OF THE INVENTION

An illustrative embodiment of the present invention provides an information processing system in which dynamic recognition of complex events is advantageously integrated with a case-based processing module.

In one aspect, an apparatus for dynamic recognition of complex events comprises at least one processing platform. The processing platform comprises at least one server, computer or other processing device having a processor coupled to a memory. The processing platform implements a plurality of modules for integration of dynamic recognition of complex events with case-based processing, the modules comprising at least a complex event processing module and a case-based processing module coupled to the complex event processing module. Event recognition in the complex event processing module triggers one or more case-based activities in the case-based processing module. The plurality of modules may further include an event preprocessing module, a proactive risk assessment and forecasting module, and a temporal associative reasoning module.

The illustrative embodiments advantageously overcome one or more of the above-noted drawbacks of conventional approaches that fail to provide adequate recognition and processing of complex events. For example, one or more of these embodiments provide an information processing system in which events originating from multiple federated information sources can be detected, normalized and combined, and the associated complex event processing integrated with a case-based processing module of the system, thereby reducing the cost and time associated with deployment of event processing functionality. Also, the need for human intervention in exception handling is considerably reduced in such an embodiment. In addition, one or more of the illustrative embodiments can be configured to provide other significant advantages, such as improved workflow routing, early detection of risk, and better temporal-based decisions.

These and other features and advantages of the present invention will become more readily apparent from the accompanying drawings and the following detailed description.

BRIEF DESCRIPTION OF THE DRAWINGS

FIG. 3 is a flow diagram illustrating exemplary processing operations performed by the FIG. 1 system in an illustrative embodiment.

DETAILED DESCRIPTION

The present invention will be described herein with reference to exemplary information processing systems and associated servers, computers, storage devices and other processing devices. It is to be appreciated, however, that the invention is not restricted to use with the particular illustrative system and device configurations shown. Moreover, the term "information processing system" as used herein is intended to be broadly construed, so as to encompass, for example, private or public cloud computing or storage systems, as well as other types of systems comprising distributed virtual infrastructure. However, a given embodiment need not comprise distributed virtual infrastructure, and may more generally comprise any arrangement of one or more processing devices.

Figure 1:
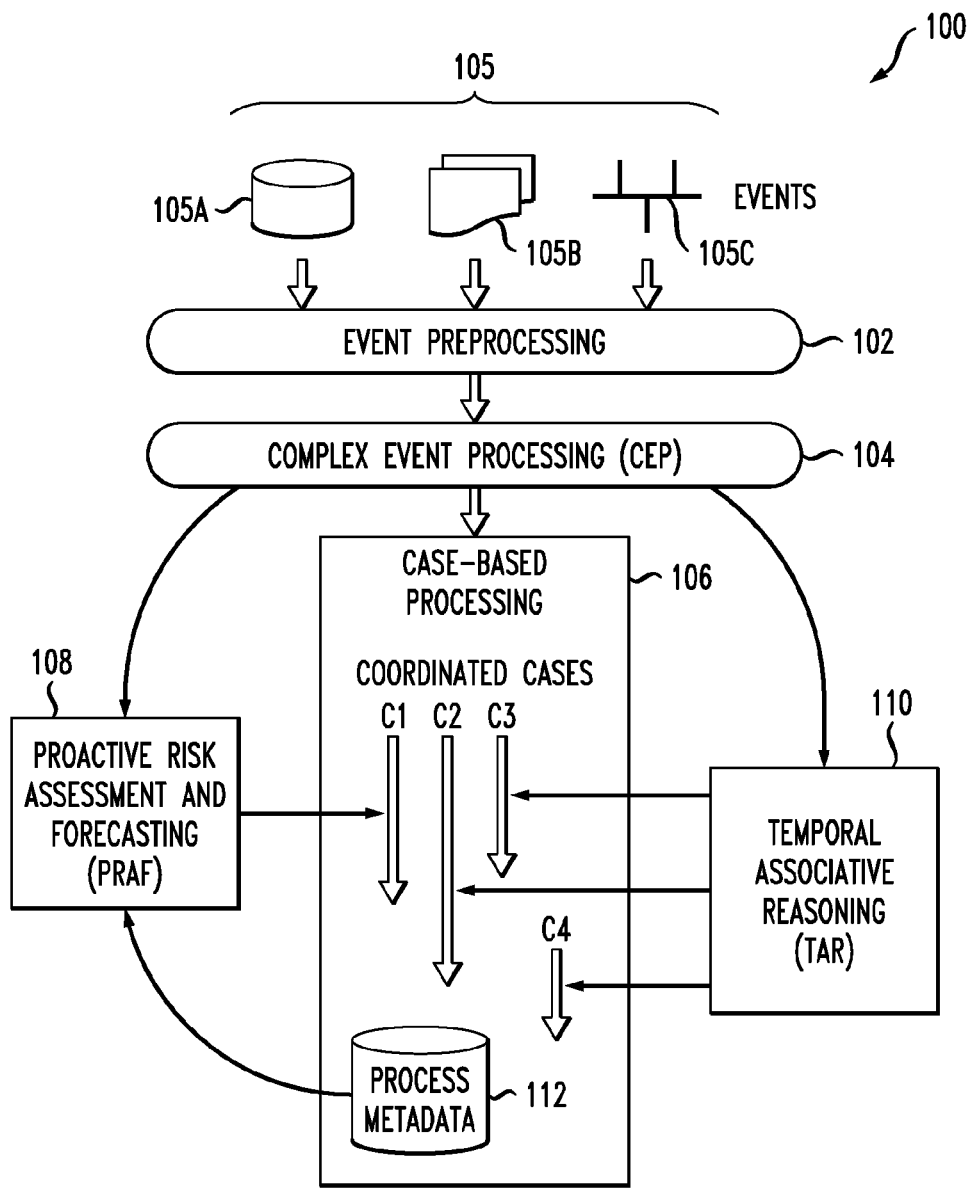
FIG. 1 shows an information processing system that integrates dynamic recognition of complex events with case-based processing.

FIG. 1 shows an information processing system 100 configured in accordance with an illustrative embodiment of the present invention. The information processing system 100 comprises an event preprocessing module 102 coupled to a complex event processing (CEP) module 104. The event preprocessing module 104 interacts with multiple event sources 105, which may include, for example, storage systems 105A, file systems 105B and event notification systems 105C, or other types of event sources, in any combination. The event preprocessing module 102 detects, normalizes and propagates events from these multiple sources 105. The events may be "federated" events, that is, events that originate from autonomous sources, where such sources may, but need not, interact with one another.

The detected events after normalization are propagated to the complex event processing module 104, which interacts with a number of other modules of the system 100, including a case-based processing module 106, a proactive risk assessment and forecasting (PRAF) module 108, and a temporal associative reasoning (TAR) module 110. The case-based processing module 106 comprises a store 112 of process metadata that is also utilized by the proactive risk assessment and forecasting module 108.

The complex event processing module 104 is configured to recognize meaningful complex events in the preprocessed event information it receives from the event preprocessing module 102. The case-based processing module 106 coordinates multiple cases each triggered by one or more complex events. In this embodiment, the coordinated cases comprise cases denoted C1, C2, C3 and C4.

The case-based processing module 106 may comprise at least a portion of an otherwise conventional case management system (CMS) such as the xCelerated Composition Platform (xCP) commercially available from EMC Corporation of Hopkinton, Mass. The process metadata 112 may be associated with a Business Activity Monitor (BAM) of xCP. The xCP CMS allows users to build and deploy case-based applications that automate business processes and coordinate content flow. These and other commercially-available CMSs are being utilized for applications such as customer care, loan origination, claims processing, new account establishment, virtual public records, public sector case management, and many others.

A given CMS as implemented within case-based processing module 106 of system 100 may comprise, by way of example, a compositional platform for visualization and management of flows, dependencies, temporal relationships, and risks, as well as associated analytics, transformers, alert publishers and alert subscribers.

In a conventional CMS, case-based workflows are generally triggered by simple events such as, for example, the arrival of a form, email, fax or other communication, or the adding of data to a database. Existing CMSs have not heretofore been driven, in a coordinated fashion, by the recognition of complex events. This impedes their effectiveness, restricts their application, limits their flexibility, and reduces their automation.

The illustrative embodiment of FIG. 1 overcomes the above-noted significant drawbacks of conventional arrangements by providing an improved arrangement in which complex event processing is integrated with case-based processing. For example, complex events recognized in complex event processing module 104 can initiate new cases in case-based processing module 106, can trigger a coordinated set of workflows within these cases, and can influence ongoing workflows. This may be accomplished at least in part by providing one or more sideband channels of events into the workflows of the case-based processing module 106. In the system 100, the complex event processing module 104 recognizes and feeds complex events into the case-based processing module 106. The modules 108 and 110 similarly serve to provide event-related inputs to the case-based processing module 106, as described below.

The proactive risk assessment and forecasting module 108 utilizes event information received from the complex event processing module 104 and process metadata from store 112 to improve the decision-making process in case-based processing module 106, as well as to initiate new cases for handling by that module. The proactive risk assessment and forecasting module 108 may comprise or utilize, by way of example, an RSA Risk Engine from RSA, the Security Division of EMC Corporation, and can be configured to generate alerts based on proactive scoring and prediction of risks from statistical analysis of process data and metadata. These alerts can be used by the case-based processing module 106 to improve decision making within cases, alter process graphs, initiate new cases, or broaden existing case-based activities.

Although the proactive risk assessment and forecasting module 108 is shown in FIG. 1 as being coupled between the complex event processing module 104 and the case-based processing module 106, this particular arrangement is not required. For example, in other embodiments, the module 108 may interact only with module 106.

The temporal associative reasoning module 110 utilizes time-based information received from the complex event processing module 104 to facilitate case coordination in the case-based processing module 106. For example, it may modify process graphs by analyzing arrival and non-arrival of particular events. Such modification of process graphs may include choosing between a number of conflicting inputs. The temporal associative reasoning module therefore provides an ability to analyze the arrival and non-arrival of events associated with a case to dynamically modify processes or workflows within the case. These and other types of heuristic reasoning about event states may trigger a request to gather information that meets case exit criteria, or may recognize an event state for which workflow should be propagated to the next appropriate step. As a result, the system 100 may be configured to support reasoned shortcuts in existing workflows that would be difficult to code and maintain in purely descriptive processes. The use of temporal associative reasoning thereby facilitates the provision of dynamic process management within the case-based processing module 106. The temporal associative reasoning module 110 may be positive or negative reinforcing, and may implement costing algorithms to provide cost weighting, or may utilize other types of rules-based processing based on temporal data.

Each of the modules 108 and 110 may be viewed as part of the above-noted sideband channel of events that influences case-based activities and workflows in the case-based processing module 106. For example, module 108 raises events associated with risk recognition and forecasting. Other modules of the system 100, such as module 104, may also comprise part of the sideband channel.

One or both of the modules 108 and 110 may utilize a set of alignment points in conjunction with one or more vector engines in order to move a vector towards a designated goal which may be broken into multiple sub-goals. The vector may comprise an n-dimensional vector where n denotes the number of potential outcomes.

It should also be noted that one or both of the modules 108 and 110 may each also be viewed as a type of complex event processing module that may be provided along with module 104 by a common event processing system.

In the system 100, taps and filters on a stream of information, which can be viewed as low-level event messages, permit correlations and analyses that lead to the recognition of complex events. Such recognition in turn supports the coordinated application of policy by multiple processing components, which may modify messages within the stream, filter or re-arrange the stream of messages, or initiate new processes to act on recognized events based on policy. The above-noted sideband channel may comprise the complex events as well as other associated information, such as hints by processing components, injected references to contextually-determined processing, etc. Such a sideband channel enables coordination of multiple workflow streams within the CMS of case-based processing module 106 with respect to events. The multiple workflow streams define multiple domains of activity that are not fully independent but are instead using complex events to collaborate with one another. Some of the workflows may have been co-launched because they were initially triggered by the same complex event. For example, two or more of the coordinated cases C1 through C4 in the module 106 of FIG. 1 may have been triggered together. However, workflows that may not have been triggered together may still be subject to ongoing coordination based on incoming events and related information.

Accordingly, the present embodiment provides a sideband channel of complex events, with case-based workflows or other activities in module 106 being initiated or modified based on this sideband channel. The system 100 in this embodiment may be viewed as a recursive system, in that events initiate and modify workflows, and processing applied to workflows, such as that applied in modules 108 and 110, leads to generation of new events.

As described above, the modules 102, 104, 106, 108 and 110 collectively provide initial detection, normalization and propagation of federated events, complex event processing capabilities, and a case management platform for solutions where dynamic event recognition is a prerequisite to triggering multiple case-based activities. The case management platform is supplemented with temporal associative reasoning to dynamically modify process graphs for these activities, and risk assessment and forecasting capabilities to generate proactive alerts based on process data and metadata.

The system 100 in the present embodiment therefore includes functionality to detect, normalize and combine external federated information, to initiate and track multiple coordinated cases from sophisticated understanding of external events, and to improve decisions within cases using proactive risk assessment and temporal associative reasoning. Case flows can be modified dynamically through analysis of event arrival and non-arrival. The functionality of the case-based processing module 106 is thus significantly enhanced by configuring that module for interaction with the other modules 104, 108 and 110 of the system, thereby reducing the cost and time associated with deployment of event processing functionality. Also, the need for human intervention in exception handling is considerably reduced. Furthermore, the system provides a number of other significant advantages, such as, for example, improved workflow routing, early detection of risk, and better temporal-based decisions.

The various modules 102, 104, 106, 108 and 110 of information processing system 100 may be implemented at least in part using public or private cloud infrastructure, or other distributed virtual infrastructure. Such a distributed virtual infrastructure may comprise, by way of example, a hypervisor platform and associated virtual processing and storage elements. An example of a commercially available hypervisor platform suitable for use in an embodiment of the invention is the VMware® vSphere™ which includes vCenter™. The distributed virtual infrastructure may further comprise one or more distributed processing platforms that include hardware products such as Celerra® and CLARiiON®, both commercially available from EMC Corporation of Hopkinton, Mass.

It is to be appreciated that the particular arrangement of elements shown in FIG. 1 is presented by way of illustrative example only, and in other embodiments different arrangements of additional or alternative elements may be used. Moreover, the functionalities associated with separate elements in the FIG. 1 embodiment may be combined into a lesser number of elements each of which performs multiple functions. Thus, at least a subset of the elements may be collectively implemented on a common processing platform, or each such element may be implemented on a separate processing platform comprising one or more servers, computers or other processing devices.

Figure 2:
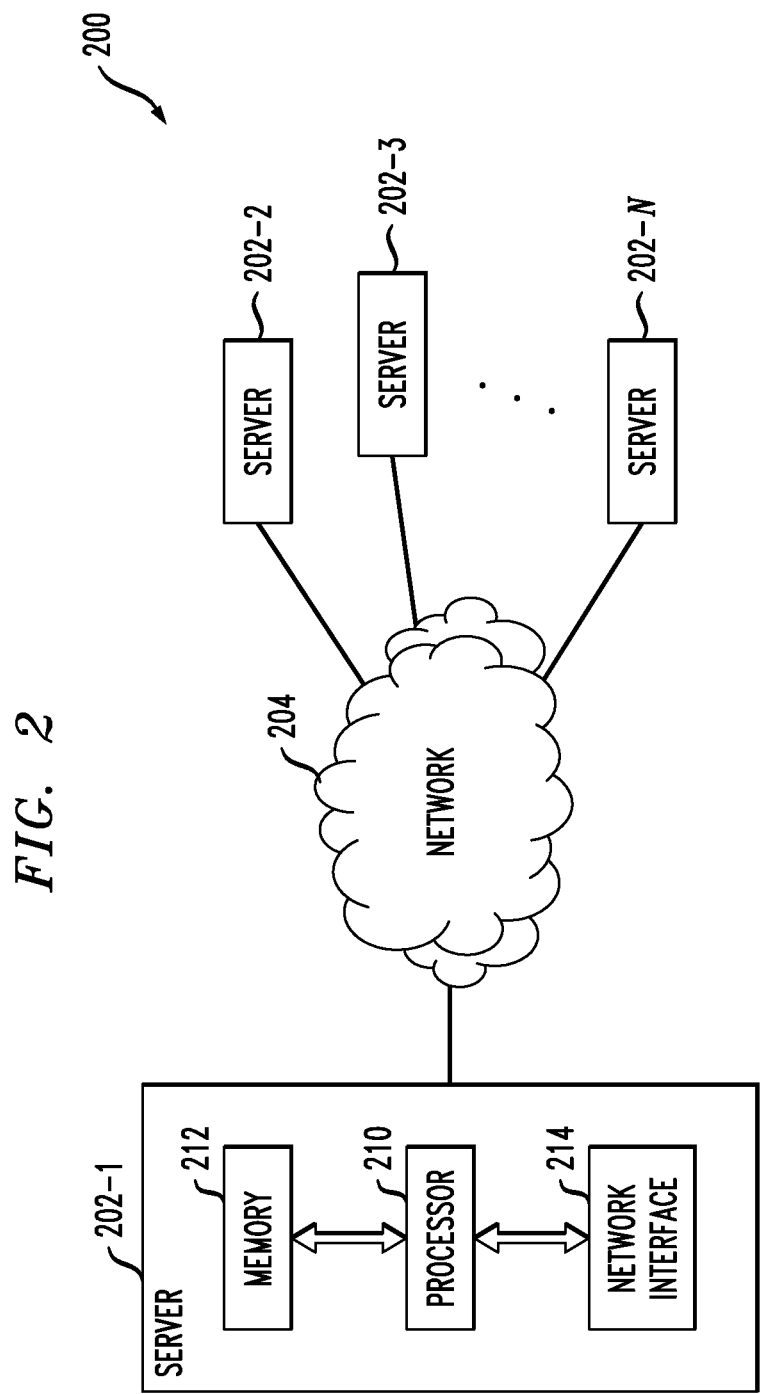
FIG. 2 shows an exemplary processing platform that implements at least a portion of the FIG. 1 system.

An example of such a processing platform is processing platform 200 shown in FIG. 2. The processing platform 200 in this embodiment comprises at least a portion of the system 100 and includes a plurality of servers, denoted 202-1, 202-2, 202-3, . . . 202-N, which communicate with one another over a network 204. One or more of the modules 102, 104, 106, 108 or 110 of system 100 may therefore each run on a server, computer or other processing platform element, which may be viewed as an example of what is more generally referred to herein as a "processing device." As illustrated in FIG. 2, such a device generally comprises at least one processor and an associated memory, and implements one or more functional modules for controlling certain features of the information processing system 100. For example, the server 202-1 in the processing platform 200 comprises a processor 210 coupled to a memory 212. Again, multiple elements may be implemented by a single processing device in a given embodiment.

The processor 210 of server 202-1 may comprise a microprocessor, a microcontroller, an application-specific integrated circuit (ASIC), a field programmable gate array (FPGA) or other type of processing circuitry, as well as portions or combinations of such circuitry elements. The memory 212 may be viewed as an example of what is more generally referred to herein as a "computer program product" having executable computer program code embodied therein. Such a memory may comprise electronic memory such as random access memory (RAM), read-only memory (ROM) or other types of memory, in any combination. The computer program code when executed by a processing device such as the server 202-1 causes the device to perform functions associated with one or more of the modules 102, 104, 106, 108 and 110, or portions thereof. One skilled in the art would be readily able to implement such software given the teachings provided herein. Other examples of computer program products embodying aspects of the invention may include, for example, optical or magnetic disks.

Also included in the server 202-1 is network interface circuitry 214, which is used to interface the server with the network 204 and other system components. Such circuitry may comprise conventional transceivers of a type well known in the art.

The other servers 202 of the processing platform 200 are assumed to be configured in a manner similar to that shown for server 202-1 in the figure.

The processing platform 200 shown in FIG. 2 may comprise additional known components such as batch processing systems, parallel processing systems, physical machines, virtual machines, virtual switches, storage volumes, etc. Again, the particular processing platform shown in the figure is presented by way of example only, and system 100 may include additional or alternative processing platforms, as well as numerous distinct processing platforms in any combination.

It should be understood that a given embodiment of the system 100 may include multiple instances of the modules 102, 104, 106, 108 and 110, and other system elements, although only single instances of such elements are shown in the system diagram for clarity and simplicity of illustration.

Also, numerous other arrangements of servers, computers, storage devices or other components are possible in the information processing system 100. Such components can communicate with other elements of the information processing system 100 over any type of network, such as a wide area network (WAN), a local area network (LAN), a satellite network, a telephone or cable network, or various portions or combinations of these and other types of networks.

An exemplary set of processing operations that may be implemented in the information processing system 100 will now be described in greater detail with reference to the flow diagram of FIG. 3. These operations include steps 300 through 308, and although shown in a serial arrangement, one or more of the steps may be performed at least in part concurrently with one or more other steps.

In step 300, the event preprocessing module 102 detects, normalizes and combines multiple events to form at least one complex event. This complex event is recognized in complex event processing module 104, as indicated in step 302. In addition to the event being recognized, it is also shown as being characterized in this embodiment. Such event recognition and characterization may comprise, for example, classification of the event against various event categories. However, terms such as "recognition" and "recognizing" as used herein are intended to be construed broadly, and in other embodiments may be viewed as incorporating classification or other types of event characterization.

In step 304, one or more case-based activities are triggered in case-based processing module 106 responsive to the above-noted recognition and characterization of the complex event in step 302. One or more alerts are then generated in step 306 based on process metadata 112 of the case-based processing module 106 in proactive risk assessment and forecasting module 108. In step 308, at least one process graph associated with the one or more case-based activities of the case-based processing module is dynamically modified under control of the temporal associative reasoning module 110.

It is to be appreciated that the particular processing operations shown in FIG. 3 are presented by way of illustrative example only, and additional or alternative operations may be used in other embodiments, as well as different orderings of the various operations.

The information processing system 100 of FIG. 1 can be used in a wide variety of different applications. A number of exemplary applications will be described in greater detail below. These exemplary applications include counter-terrorism systems, virtual data center (VDC) security and compliance, fraud detection in financial services, health care information management, and quality control for manufacturing. In these and other applications, the complex event processing module 104 is utilized to infer situations from interrelated and interdependent events, and to initiate coordinated and possibly urgent case-based activities in the case-based processing module 106.

In a counter-terrorism system application, detection in the complex event processing module 104 of a burst of electronic activity by suspected terrorists related to a potential target can initiate rapid planning and approval for increased surveillance, start a process to heighten security at the target and similar targets, and trigger aggregation of relevant data for further decision making and synchronization, all as case-based workflows within the case-based processing module 106. Additionally, the scoring of risk profiles in the proactive risk assessment and forecasting module 108 can differentiate communications within a terrorist network from those within a social network.

In a VDC security and compliance application, detection in the complex event processing module 104 of an attempted intrusion or denial-of-service attack in the VDC triggers case-based processes in the case-based processing module 106 to raise authentication levels, limit all but essential processing, start a workflow to look for similar incidents, and circulate a fast-tracked resource request. Additionally, the proactive risk assessment and forecasting module 108 can provide assessments of risk or state, such as data leakage likelihood or predictions of imminent failure, and such assessments can be used to trigger case creation or escalation.

In a financial services fraud detection application, the complex event processing module 104 can detect patterns of events indicating possible fraud, from credit card misuse, to money laundering via commodities trading, to international schemes for off-the-books money transfers. Once the events are known, multiple processes are initiated as respective cases within the case-based processing module 106 to limit exposure, escalate investigations, and contact suspected victims and responsible authorities. Additionally, the proactive risk assessment and forecasting module 108 can be configured to detect double payments in a database within or otherwise accessible to module 106, representing financial loss and potential fraud, since the same payment request may be sent to an organization by a service provider several times using different methods (e.g., mail, fax, email).

In a health care information management application, semantic technologies for schema alignment and normalization may be used to improve the process of injecting heterogeneous information sets into an event space of the complex event processing module 104 and to trigger cases within the case-based processing module 106. Loosely federated health care systems have varying approaches to defining identities of patients, physicians and providers, and capture different attributes regarding diagnoses, tests, multimedia artifacts (e.g., scans) and treatment histories. The system 100 allows the normalized events to be more consistently and coherently processed by the modules 104 and 106. The ensuing process logic can derive from information events, rather than vice-versa, enabling new flexibility in separating information sets (e.g., forms, folders, associated documents) from the processing workflows that are already well handled by a case management system. The temporal associative reasoning module 110 may be configured to reconcile multiple time windows in which a patient received specific prescription drugs, and to detect or reject possible interactions from simultaneous use of these drugs. It could also direct changes in the appropriate process workflow responsive to late receipt of an out-of-date test result. The proactive risk assessment module 108 can add sophistication to the case management system in areas such as cross-case analysis of the likelihood of a disease pandemic; exceeding a threshold here can trigger a new "umbrella" case to orchestrate and coordinate responses.

In a manufacturing quality control application, the various modules of the system 100 may be configured to perform operations such as quality control, root cause analysis, and the detection of patterns in demand traced to manufacturing workflows. Trend analysis may be performed by the complex event processing module 104 operating on information feeds or by proactive risk assessment and forecasting module 108 operating on the knowledge base of cases within the case-based processing module 106. Such trend analysis can detect product weaknesses and faulty batches, triggering workflows for investigation of manufacturing processes and even product warnings or recalls.

The above applications are exemplary only, and the system 100 can of course be utilized in numerous other applications.

The illustrative embodiments provide numerous advantages over conventional techniques. For example, one or more of these embodiments integrate complex event recognition with a case management system such as xCP. External complex event processing, based on normalized, federated information, leads to coordinated case creation and processing. Internal scoring and risk prediction leverages the considerable data available within the case management system to make cross-case inferences and predictions that improve business decisions and focus attention where it is needed. Multiple complex event processing products can be configured to process normalized feeds from federated information systems, and these products can be easily incorporated as front-ends into case-based workflows and processes in the case management system. The addition of temporal and associative rule-based reasoning against events further improves the way that case-based business process workflows are architected, enabling the automation of substantially more complex systems that are easier to systematically develop and test.

A given embodiment advantageously provides an information-centric platform in which business information becomes the driver for enterprise processes. Such a platform may be configured to support naturally asynchronous arrival of information, complex integration of information in support of enterprise processes (but not necessarily tightly coupled to them), development of dependent information graphs for the initiation or continuation of case-based enterprise processes, adjustments to these process priorities and sequencing based on event arrival (or non-arrival) and time-based reasoning, callouts to complex event processing for information assessment needed for routing or case management system step execution, execution of risk assessment and forecasting to improve risk event detection and prediction, and hence proactive decision making within the case management system, and synchronization of case-based processes of the case management system based on continued information gathering and event recognition. An information associative graph may be generated that can be reasoned against for completeness or conversely for gaps. This reasoning step would enable a process decision to be made (i.e., a determination of the next step), based upon the available information and the goal that the rule is seeking. In this way, fine grained process steps can be driven by the complex event processing and proactive risk assessment modules as a decision engine for determining next steps toward goal completion.

As indicated previously, functionality such as that described in conjunction with the system diagram of FIG. 1 and the flow diagram of FIG. 3 can be implemented at least in part in the form of one or more software programs stored in memory and executed by a processor of a processing device such as a computer or server. A memory having such program code embodied therein is an example of what is more generally referred to herein as a "computer program product."

It should again be emphasized that the above-described embodiments of the invention are presented for purposes of illustration only. Many variations may be made in the particular arrangements shown. For example, although described in the context of particular system and device configurations, the techniques are applicable to a wide variety of other types of information processing systems, processing devices and information technology infrastructure arrangements. In addition, any simplifying assumptions made above in the course of describing the illustrative embodiments should also be viewed as exemplary rather than as requirements or limitations of the invention. Numerous other alternative embodiments within the scope of the appended claims will be readily apparent to those skilled in the art.

What is claimed is:

1. An apparatus comprising:
   at least one processing platform comprising at least one processing device having a processor coupled to a memory, wherein the processing platform implements a plurality of modules for integration of dynamic recognition of complex events with case-based processing, the modules comprising:
   a complex event processing module;
   a case-based processing module coupled to the complex event processing module; and
   a proactive risk assessment and forecasting module coupled to at least one of the complex event processing module and the case-based processing module;
   wherein complex event recognition in the complex event processing module triggers one or more case-based activities in the case-based processing module;
   wherein a given complex event comprises one or more component events, the one or more case-based activities triggered for the given complex event being based at least in part on an analysis of arrival and non-arrival of the one or more component events associated with the given complex event; and
   wherein the proactive risk assessment and forecasting module generates one or more alerts based on process metadata of the case-based processing module.

2. The apparatus of claim 1 wherein the case-based processing module coordinates multiple cases each triggered by one or more complex events recognized by the complex event processing module.

3. The apparatus of claim 1 wherein the case-based processing module comprises a case management system.

4. The apparatus of claim 3 wherein the case management system comprises a compositional platform for visualization and management of one or more of flows, dependencies, temporal relationships, and risks, and one or more of associated analytics, transformers, alert publishers and alert subscribers.

5. The apparatus of claim 3 wherein the case management system comprises an xCelerated Composition Platform (xCP).

6. The apparatus of claim 1 wherein the plurality of modules further comprises an event preprocessing module that detects, normalizes and combines multiple component events to form a complex event for handling by the complex event processing module.

7. The apparatus of claim 6 wherein the multiple component events processed by the event preprocessing module comprise federated events received from respective federated information sources.

8. The apparatus of claim 1 wherein the proactive risk assessment and forecasting module initiates at least one case in the case-based processing module.

9. The apparatus of claim 1 wherein the plurality of modules further comprises a temporal associative reasoning module coupled to at least one of the complex event processing module and the case-based processing module.

10. The apparatus of claim 9 wherein the temporal associative reasoning module dynamically modifies at least one process graph associated with said one or more case-based activities in the case-based processing module, the dynamic modification comprising selecting between a plurality of conflicting inputs.

11. The apparatus of claim 9 wherein the temporal associative reasoning module initiates at least one case in the case-based processing module.

12. The apparatus of claim 9 wherein the temporal associative reasoning module utilizes time-based information received from the complex event processing module to facilitate case coordination in the case-based processing module by analyzing the arrival and non-arrival of particular component events expected to be associated with the given complex event.

13. The apparatus of claim 9 wherein the temporal associative reasoning module dynamically modifies a process graph associated with the one or more case-based activities in the case-based processing module, the dynamic modification comprising configuring one or more reasoned shortcuts in an existing workflow of case-based activities.

14. The apparatus of claim 1 wherein the processing platform is implemented at least in part utilizing distributed virtual infrastructure.

15. The apparatus of claim 1 wherein the proactive risk assessment and forecasting module utilizes the one or more alerts to dynamically modify the one or more case-based activities triggered for the given complex event.

16. A method comprising the steps of:
recognizing a complex event in a complex event processing module;
triggering one or more case-based activities in a case-based processing module coupled to the complex event processing module responsive to said recognizing step; and
generating one or more alerts based on process metadata of the case-based processing module in a proactive risk assessment and forecasting module coupled to at least one of the complex event processing module and the case-based processing module;
wherein a given complex event comprises one or more component events, the one or more case-based activities triggered for the given complex event being based at least in part on an analysis of arrival and non-arrival of the one or more component events associated with the given complex event.

17. The method of claim 16 further comprising the steps of detecting, normalizing and combining multiple component events in an event preprocessing module to form a complex event for handling by the complex event processing module.

18. The method of claim 16 further comprising the step of dynamically modifying at least one process graph associated with said one or more case-based activities in a temporal associative reasoning module coupled to at least one of the complex event processing module and the case-based processing module.

19. A computer program product comprising a non-transitory processor-readable storage medium having encoded therein executable code of one or more software programs, wherein the one or more software programs when executed by a processing platform implement the steps of the method of claim 16.

20. An information processing system comprising:
a plurality of information sources generating events; and
at least one processing platform coupled to the information sources, wherein the processing platform implements a plurality of modules for integration of dynamic recognition of complex events with case-based processing, the modules comprising:
a complex event processing module;
a case-based processing module coupled to the complex event processing module; and
a proactive risk assessment and forecasting module coupled to at least one of the complex event processing module and the case-based processing module;
wherein complex event recognition in the complex event processing module triggers one or more case-based activities in the case-based processing module;
wherein a given complex event comprises one or more component events, the one or more case-based activities triggered for the given complex event being based at least in part on an analysis of arrival and non-arrival of the one or more component events associated with the given complex event; and
wherein the proactive risk assessment and forecasting module generates one or more alerts based on process metadata of the case-based processing module.

21. The system of claim 20 wherein the processing platform comprises a plurality of servers interconnected via a network.

* * * * *